(12) United States Patent
Fujikura

(10) Patent No.: US 8,033,988 B2
(45) Date of Patent: Oct. 11, 2011

(54) ENDOSCOPE WITH ANGLED INFLATION CHANNEL

(75) Inventor: Tetsuya Fujikura, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1024 days.

(21) Appl. No.: 11/342,591

(22) Filed: Jan. 31, 2006

(65) Prior Publication Data

US 2006/0195016 A1    Aug. 31, 2006

(30) Foreign Application Priority Data

Feb. 28, 2005    (JP) ............... P.2005-053909

(51) Int. Cl.
*A61B 1/00* (2006.01)
*A61B 1/04* (2006.01)
*A61B 1/12* (2006.01)

(52) U.S. Cl. ............... 600/116; 600/129; 600/156

(58) Field of Classification Search ............... 600/114, 600/104, 106, 107, 115–116, 128, 129, 153, 600/155–158; 604/95.01–102.03
See application file for complete search history.

(56) References Cited

U.S. PATENT DOCUMENTS

| 4,224,929 A | 9/1980 | Furihata |
| 6,149,598 A * | 11/2000 | Tanaka ............... 600/462 |

FOREIGN PATENT DOCUMENTS

| DE | 10 2004 023 457 A1 | 12/2004 |
| JP | 03-284265 A | 12/1991 |
| JP | 8-280686 A | 10/1996 |
| JP | 11-290263 A | 10/1999 |
| JP | 2001-299686 | 10/2001 |
| JP | 2002-301019 A | 10/2002 |
| JP | 2004-329645 A1 | 11/2004 |

* cited by examiner

*Primary Examiner* — Matthew J Kasztejna
*Assistant Examiner* — Ryan Henderson
(74) *Attorney, Agent, or Firm* — Birch, Stewart, Kolasch & Birch, LLP

(57) ABSTRACT

An endoscope apparatus comprises: an endoscope comprising an insertion portion, wherein an air hole is formed at a distal end of the insertion portion; and a balloon attached to the distal end of the insertion portion, the balloon being expanded by supply of air through an inlet/outlet port of the air hole and contracted by suction of air through of the inlet/outlet port, wherein the inlet/outlet port of the air hole is formed to be inclined at a predetermined angle to an axis of the insertion portion of the endoscope.

3 Claims, 6 Drawing Sheets

ENDOSCOPE WITH ANGLED INFLATION CHANNEL

BACKGROUND OF THE INVENTION

1. Field of the Invention

The present invention relates to an endoscope apparatus, in particular, an endoscope apparatus for observing the alimentary canal at the depths such as intestinum tenue, large intestine, etc., in which balloons are attached to the distal end of the endoscope insertion portion.

2. Description of the Related Art

Where the insertion portion of an endoscope is inserted into the alimentary canal at the depths such as intestinum tenue, etc., it is difficult to transmit a force to the distal end of the insertion portion due to complicated bending of intestinal tracts only by pushing and inserting the insertion portion thereinto, wherein it is difficult to insert the insertion portion into the depths. For example, if excess bending and deflection are brought about at the insertion portion, it becomes impossible to insert the insertion portion further into the depths. Therefore, such an operation method has been proposed, in which the insertion portion of an endoscope is inserted into an insertion assisting member and is then inserted into a body cavity, and the insertion portion is inserted into the depths while preventing excess bending and deflection of the insertion portion by guiding the insertion portion by means of the insertion assisting member.

For example, JP-A-2002-301019 discloses an endoscope apparatus in which a first balloon is mounted at the distal end of the endoscope insertion portion, and simultaneously, a second balloon is mounted at the distal end of the insertion assisting member (a so called over-tube or sliding tube).

By expanding the first balloon and bringing the same into contact with the inner wall of the intestine, it is possible to provisionally fix the distal end of the insertion portion in an intestinal tract. Similarly, by expanding the second balloon, it becomes possible to provisionally fix the distal end of the insertion assisting member in the intestinal tract. Therefore, by inserting the insertion portion and the insertion assisting member by turns and hauling in the same while causing the first balloon and the second balloon to expand and contract, the insertion portion can be inserted into the depths of a complicated and bent intestinal tract such as an intestinum tenue.

Also, the first balloon of JP-A-2002-301019 is connected to an air tube via the inlet/outlet port of the air hole formed at the distal end of the insertion portion, wherein the first balloon is expanded with air supplied through the air tube and is caused to contract with air sucked in via the air tube. The inlet/outlet port of the air hole and the air tube are cleansed by the balloon being removed after use.

In this connection, in the endoscope apparatus according to JP-A-2002-301019, the inlet/outlet port of the airhole for supplying air into the first balloon is formed in the direction orthogonal to the axis of the insertion portion of the endoscope. That is, since the air tube disposed along the axis of the insertion portion is coupled to the inlet/outlet port of the air hole at a right angle, it was difficult for a brush to be inserted into the air tube through the inlet/outlet port of the air hole when cleansing the inlet/outlet port of the air hole and the air tube. Therefore, in the endoscope apparatus according to JP-A-2002-301019, brush cleansing could not be carried out, wherein there was a problem in that the cleansing was dependent only on a drug solution.

SUMMARY OF THE INVENTION

The invention was developed in view of the above-described situations, and it is therefore an object of the invention to provide an endoscope apparatus capable of cleansing an inlet/outlet port of a air hole and an air tube, by which air is supplied into balloons mounted at the distal end of an insertion portion thereof, by means of a brush.

In order to achieve the above-described object, according to a first aspect of the invention, there is provided an endoscope apparatus comprising: an endoscope comprising an insertion portion, wherein an air hole is formed at a distal end of the insertion portion; and a balloon attached to the distal end of the insertion portion, the balloon being expanded by supply of air through an inlet/outlet port of the air hole and contracted by suction of air through of the inlet/outlet port, wherein the inlet/outlet port of the air hole is formed to be inclined at a predetermined angle to an axis of the insertion portion of the endoscope.

In the present specification, the wording "the inlet/outlet port of the air hole is formed to be inclined at a predetermined angle to an axis of the insertion portion of the endoscope" means that a discharge/suction axis line of air at the inlet/outlet port is formed to be inclined at a predetermined angle to an axis of the insertion portion of the endoscope. The predetermined angle is more than 0° and is less than 90°.

According to the first aspect of the invention, since the inlet/outlet port of the air hole for supplying air into balloons is formed to be inclined at a predetermined angle to the axis of the insertion portion, a brush can be easily inserted into the air tube through the inlet/outlet port of the air hole, wherein it becomes possible to cleanse the inlet/outlet port of the air hole and the air tube by means of a brush. In addition, since the inlet/outlet port of the air hole is formed to be inclined, the surface opening of the inlet/outlet port of the air hole, which appears on the surface of the distal end, is made slot-like. To the contrary, in the inlet/outlet port of the related-art air hole having the same diameter, the surface opening was made circular or round in the inlet/outlet port of the related-art air hole formed in the direction orthogonal to the axis of the insertion portion. Accordingly, if the surface openings are compared with each other, the slot of the present application is larger than the related-art circular hole. Therefore, insertion efficiency of a brush is improved. Further, even in a case where a balloon having the same area is adhered to the surface opening, the air suction characteristics in the present application in which the surface opening is large are improved.

According to a second aspect of the invention, there is provided the endoscope apparatus described in the first aspect of the invention, wherein the inlet/outlet port of the air hole is connected to an air tube disposed in the endoscope insertion portion via a piping member bent at a predetermined curvature ratio.

According to the second aspect, since the inlet/outlet port of the air hole is connected to an air tube via a piping member bent at a predetermined curvature ratio, it is possible to smoothly insert a brush into the air tube through the inlet/outlet port of the air hole.

According to the third aspect of the invention, there is provided the endoscope apparatus described in the second aspect of the invention, wherein the piping member is formed so as to satisfy the conditions of $r > 5$ mm, $\theta < 60°$, and $h < d/2$ where a radius of curvature of the piping member is $r$, an attaching angle of the piping member is $\theta$, height of the piping member from an outer surface of the distal end of the insertion portion is $h$ after the piping member is attached, and an outer diameter of the distal end of the insertion portion is $d$.

In the present specification, the wording "attaching angle of the piping member" means "an angle made by: the axis of an end part of the piping member on the side of the air hole; and the axis of the insertion portion".

The wording "height of the piping member from an outer surface of the distal end of the insertion portion is h after the piping member is attached" means that a distance between: an outer surface of the distal end; and an inner circumferential face, opposite to the outer surface with respect to the central axis of the piping member, of the other end part of the piping member on the side of the air tube is h.

According to the third aspect of the invention, since a brush can be inserted into the air tube through the inlet/outlet port of the air hole, the piping member can be smoothly cleansed by means of the brush.

DETAILED DESCRIPTION OF THE INVENTION

Hereinafter, a description is given of a preferred embodiment of an endoscope apparatus according to the invention with reference to the accompanying drawings.

Figure 1:
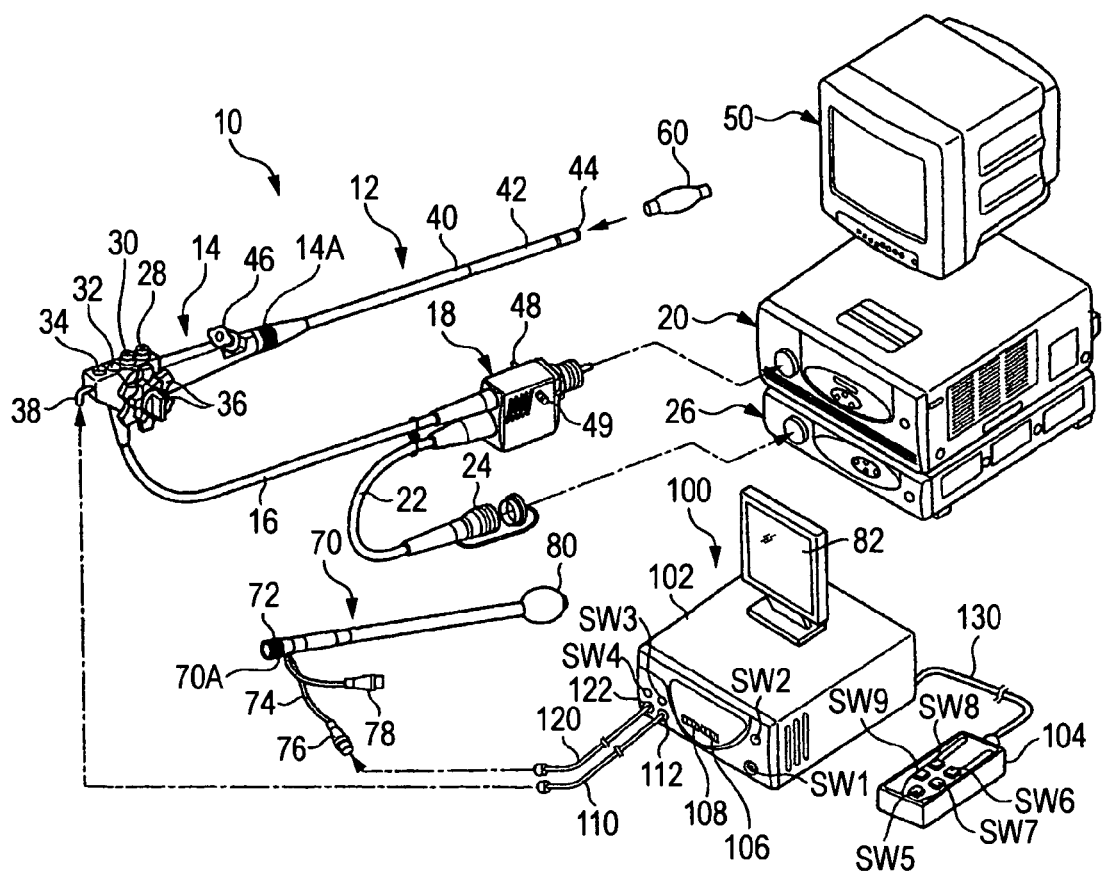
FIG. 1 is a configuration view of a system of an endoscope apparatus according to the invention.

FIG. 1 is a configuration view of a system depicting an embodiment of an endoscope apparatus according to the invention. The endoscope apparatus depicted in the same drawing is composed mainly of an endoscope 10, an insertion assisting member 70, and a balloon control unit 100.

The endoscope 10 is provided with a hand-side operation portion 14 and an insertion portion 12 that is connected to the hand-side operation portion 14 and is inserted into a body cavity. A universal cable 16 is connected to the hand-side operation portion 14, and an LG connector 18 is provided at the distal end of the universal cable 16. The LG connector 18 is detachably connected to a light source unit 20 by which illumination light is provided to an illumination optical system 54 (Refer to FIG. 2). Also, an electric connector 24 is connected to the LG connector 18 via a cable 22. The electric connector 24 is detachably coupled to a processor 26.

The hand-side operation portion 14 is concurrently provided with an air/water button 28, a suction button 30, a shutter button 32, and a function change button 34, and is also provided with a pair of angle knobs 36 and 36. A balloon air-feeding port 38 is formed of an L-shaped tube at the base portion of the hand-side operation portion 14. By feeding a fluid such as air to the balloon air-feeding port 38 and sucking air therefrom, the first balloon 60 can be caused to expand and contract.

The insertion portion 12 is composed of a flexible portion 40, a bending portion 42, and a distal end hard portion 44 in order from the hand-side operation portion 14 side. The bending portion 42 is remotely operated for bending by turning the angle knobs 36 and 36 of the hand-side operation portion 14, whereby the distal end hard portion 44 can be turned in a desired direction.

Figure 2:
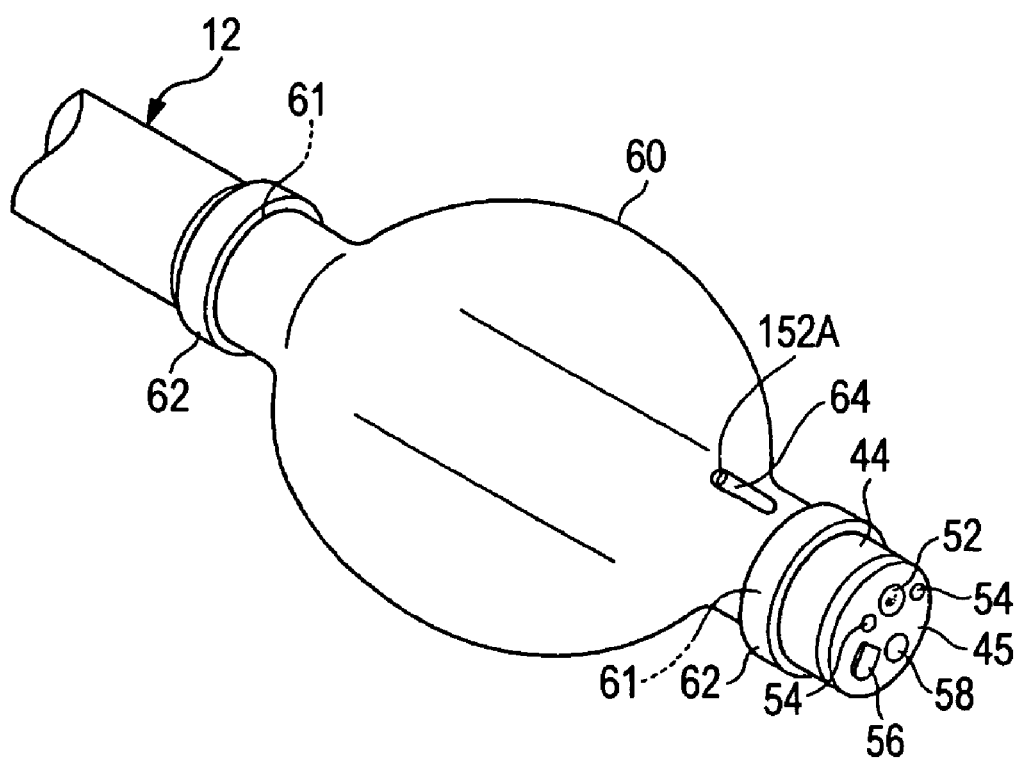
FIG. 2 is a perspective view depicting the first balloon of the insertion portion of the endoscope.
Figure 3:
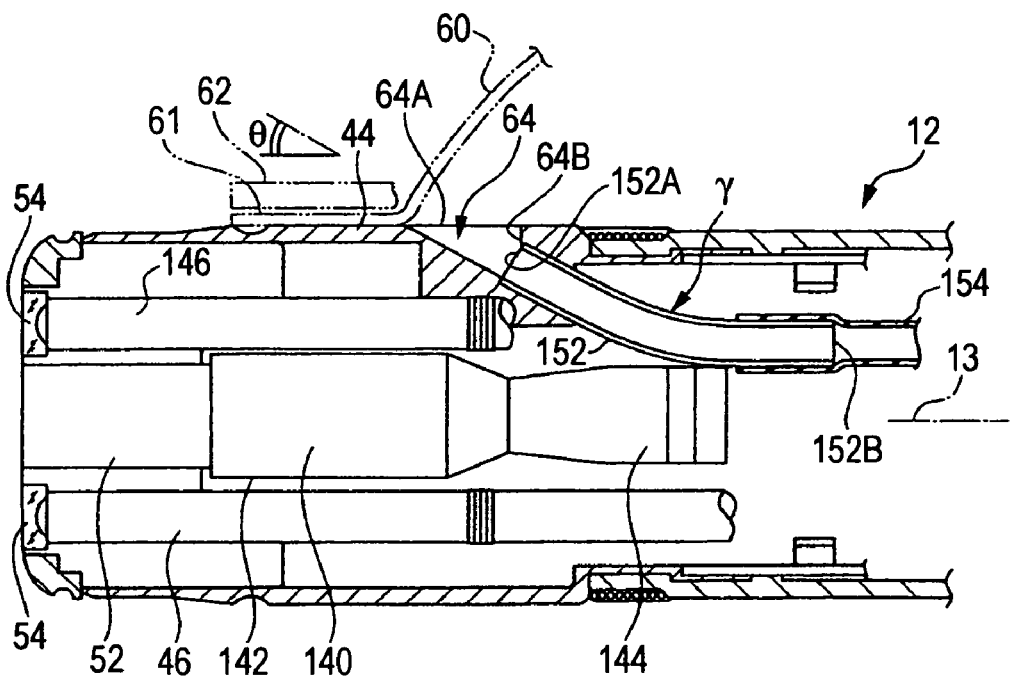
FIG. 3 is a side sectional view of the distal end hard portion of the endoscope.

As depicted in FIG. 2, an observation optical system 52, illumination optical systems 54 and 54, an air/water nozzle 56, and a forceps port 58 are, respectively, provided at predetermined positions at the distal end 45 of the distal end hard portion. A CCD 140 of FIG. 3 is disposed via a prism (not illustrated) rearward of the observation optical system 52, and a signal cable 144 is connected to a substrate 142 that supports the CCD 140. The signal cable 144 is inserted into the insertion portion 12, the hand-side operation portion 14, and the universal cable 16, etc., which are depicted in FIG. 1, are caused to extend to the electric connector 24, and is connected to the processor 26 via the electric connector 24. Therefore, an observation image picked up the observation optical system 48 is image-formed on a light-receiving surface of the CCD 140 and is converted to electric signals. The electric signals are outputted to the processor 26 via the signal cable 144 and is converted to picture signals by the picture signal processing portion of the processor 26. After that, the observation image is displayed as an observation image on a monitor 50 connected to the processor 26.

Figure 4:
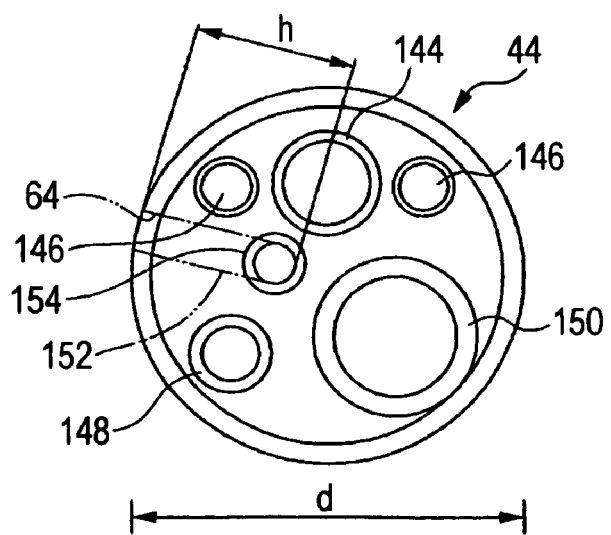
FIG. 4 is a longitudinally sectional view of the distal end hard portion of the endoscope.

The outgoing ends of a pair of light guides 146 and 146 are disposed as depicted in FIG. 3 and FIG. 4 rearward of the illumination optical systems 54 and 54 of FIG. 2. The light guides 146 and 146 are inserted into the insertion portion 12, the hand-side operation portion 14, and the universal cable 16, and the incidence ends thereof are disposed in the LG connector 18. Accordingly, by connecting the LG connector 18 to the light source unit 20, illumination irradiated from the light source unit 20 is transmitted to the illumination optical systems 54 and 54 via the light guides 146 and 146, and is irradiated forward from the illumination optical systems 54 and 54. The light guides 146 and 146 are disposed so as for the observation optical system 48 to be placed therebetween.

The air/water nozzle 56 of FIG. 2 is caused to communicate with a valve (not illustrated) operated by the air/water button 28 of FIG. 1 via an air/water channel 148. The valve is caused to communicate with the air/water connector 48 secured at the LG connector 18. Air/water feeding means (not illustrated) is connected to the air/water connector 48, by which air or water is supplied. Therefore, by operating the air/water button 28, air or water can be jetted from the air/water nozzle 56 to the observation optical system 52.

The forceps port 58 of FIG. 2 is caused to communicate with the forceps insertion portion 46 of FIG. 1 via a forceps channel 150 of FIG. 4. Therefore, by inserting treatment equipment such as forceps from the forceps insertion portion 46, the treatment equipment can be led out from the forceps portion 58. In addition, the forceps port 58 is caused to communicate with a valve (not illustrated) operated by the suction button 30. The valve is further connected to the suction connector 49 of the LG connector 18. Accordingly, by connecting sucking means (not illustrated) to the suction connector 49 and operating the valve by the suction button 30, it is possible to suck in a lesioned part through the forceps port 58.

In this connection, a first balloon 60 made of an elastic material such as rubber is mounted on the outer circumferential surface of the bending portion 42 and the distal end hard portion 44. The first balloon 60 is formed roughly cylindrical with both end parts 61 and 61 thereof narrowed down. After inserting the insertion portion 12 into the first balloon 60 and disposing the same at a desired position, and fitting rubber-made fixing rings 62 and 62 to both end parts of the first balloon 60 as depicted in FIG. 2, the first balloon 60 is fixed at the bending portion 42 and the distal end hard portion 44.

An inlet/outlet port 64 of the air hole is formed on the outer circumferential surface of the distal end hard portion 44 that becomes a forward mounting position of the first balloon 60.

The inlet/outlet port 64 of the air hole is caused to communicate with the balloon air-feeding port 38 secured at the hand-side operation portion 14 of FIG. 1 via the piping member 152 and the air tube 154 depicted in FIG. 3, and the balloon air-feeding port 38 is connected to the balloon control unit 100 via a tube 110. Therefore, since air is supplied and sucked in by the balloon control unit 100, the first balloon 60 is caused to expand and contract. In addition, the first balloon 60 expands to be roughly spherical by the supply of air, and is provided so as to be adhered to the outer surface of the distal end hard portion 44 and the bending portion 42 by suction of air. The inlet/outlet port 64 of the air hole, the piping member 152 and the air tube 154 will be described later.

On the other hand, the insertion assisting member 70 depicted in FIG. 1 is formed to be cylindrical, has a slightly larger inner diameter than the outer diameter of the insertion portion 12, and simultaneously has sufficient flexibility. A hard gripping portion 72 is provided at the base end of the insertion assisting member 70, and the insertion portion 12 is inserted through the gripping portion 72.

The second balloon 80 is mounted in the vicinity of the distal end of the insertion assisting member 70. The second balloon 80 is formed roughly cylindrical with both ends closed and is mounted in a state where it passes through the insertion assisting member 70. And, the second balloon 80 is fixed by winding thread (not illustrated) thereon. A tube 74 attached to the outer circumferential surface of the insertion assisting member 70 is caused to communicate with the second balloon 80, and a connector 76 is provided at the base end portion of the tube 74. A tube 120 is connected to the connector 76, and the tube 74 is connected to the balloon control unit 100 via the tube 120. Therefore, the second balloon 80 is caused to expand and contract by supplying and sucking in air by means of the balloon unit 100. The second balloon 80 expands roughly spherically by supply of air, and is adhered to the outer circumferential surface of the insertion-assisting tool 70 by suction of air.

An inlet 78 is provided at the base end side of the insertion assisting member 70. The inlet 78 is caused to communicate with an opening (not illustrated) formed on the inner circumferential surface of the insertion assisting member 70. Therefore, by injecting a lubricant (for example, water) by means of a syringe, etc., through the inlet 78, the lubricant can be supplied inside the insertion assisting member 70. Therefore, when the insertion portion 12 is inserted into the insertion assisting member 70, friction between the inner circumferential surface of the insertion assisting member 70 and the outer circumferential surface of the insertion portion 12 can be reduced, wherein relative movement between the insertion portion 12 and the insertion assisting member 70 can be smoothly carried out.

The balloon control unit 100 is a device that supplies air to the first balloon 60 and sucks in air therefrom, and also supplies air to the second balloon 80 and sucks in air therefrom. The balloon unit 100 is composed mainly of a unit body 102, and a hand switch 104 for remote control.

Figure 5:
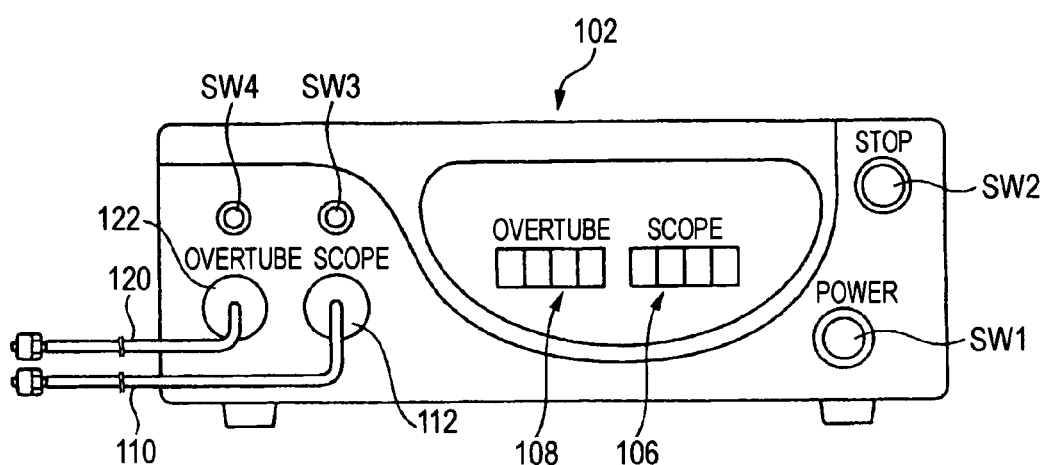
FIG. 5 is a front elevational view depicting the front side panel of the balloon control unit.

As depicted in FIG. 5, a power source switch SW1, a stop switch SW2, the first pressure display portion 106, the second pressure display portion 108, the first function stop switch SW3 and the second function stop switch SW4 are provided at the front side of the unit body 102. The first pressure display portion 106 and the second pressure display portion 108 are, respectively, panels for displaying the pressure value of the first balloon 60 and the second balloon 80. If an abnormality such as tear or breakage of the balloons occurs, the pressure display portions 106 and 108 display an error code.

The first function stop switch SW3 and the second function stop switch SW4 turn on and off the functions of the endoscope control system A and of the insertion assisting member control system B, respectively. Where only one of the first balloon 60 and the second balloon 80 is used, the function stop switch SW3 or SW4 which is not used is operated to turn off the function. In the control system A or B the functions of which are turned off, supply of air and suction thereof completely stop, and the pressure display portion 106 or 108 of the system is also turned off. By turning off both the function stop switches SW3 and SW4, default setting can be carried out, for example, by simultaneously pressing all the switches SW5 through SW9 of the hand switch 104 with both the functions top switches SW3 and SW4 turned off, calibration for the atmospheric pressure is performed.

The tube 110 for supply of air to the first balloon 60 and suction of air therefrom and the tube 120 for supply of air to the second balloon 80 and suction of air therefrom are connected to the front side of the unit body 102. At the connection portions between the respective tubes 110 and 120 and the unit body 102, a reverse flow preventing units 112 and 122 are provided in order to prevent a body fluid from reverse flow thereinto when the first balloon 60 or the second balloon 80 is broken. The reverse flow preventing unit 112 and 122 is composed by incorporating a gas liquid separation filter in a hollow disk-shaped case (not illustrated) detachably mounted in the unit body 102. Inflow of fluid into the unit body 102 is prevented by the filter.

Further, the pressure display portions 106 and 108, the function stop switches SW3, SW4 and the reverse flow preventing units 112 and 122 for the endoscope 10 and those for the insertion assisting member are always disposed in a fixed relationship. That is, the pressure display portion 106, the function stop switch SW3 and the reverse flow preventing unit 112 for the endoscope 10 are, respectively, disposed at the right side of the pressure display portion 108, the function stop switch SW4 and the reverse flow preventing unit 122 for the insertion assisting member 70.

On the other hand, the hand switch 104 is provided with a stop switch SW5 similar to the stop switch SW2 at the unit body 102 side, an ON/OFF switch SW6 for instructing pressurization and pressure reduction of the first balloon 60, a pause switch SW7 for holding the pressure of the first balloon 60, an ON/OFF switch SW8 for instruction pressurization and pressure reduction of the second balloon 80, and a pause switch SW9 for holding the pressure of the second balloon 80. The hand switch 104 is electrically connected to the unit body 102 via a cord 130. Also, although not illustrated in FIG. 1, the hand switch 104 is provided with a display portion for showing an air feeding state and an exhaust state of the first balloon 60 or the second balloon 80.

The balloon control unit 100 thus composed expands the balloons 60 and 80 by feeding air thereinto, and holds the air pressure at a fixed value to keep the balloons 60 and 80 in an expanded state. In addition, the balloon control unit 100 causes the respective balloons 60 and 80 to contract by suction air therefrom and keeps the respective balloons 60 and 80 in a contracted state by controlling the air pressure at a fixed value.

The balloon control unit 100 is connected to a monitor 82 exclusive for the balloons, and when the respective balloons 60 and 80 are caused to expand and contract, the pressure values, expansion and contraction states of the respective balloons 60 and 80 are displayed on the exclusive monitor 82. Also, the pressure value, expansion and contraction states of the respective balloons 60 and 80 maybe superimposed in an observation image of the endoscope 10 and may be displayed therein.

Figure 6:
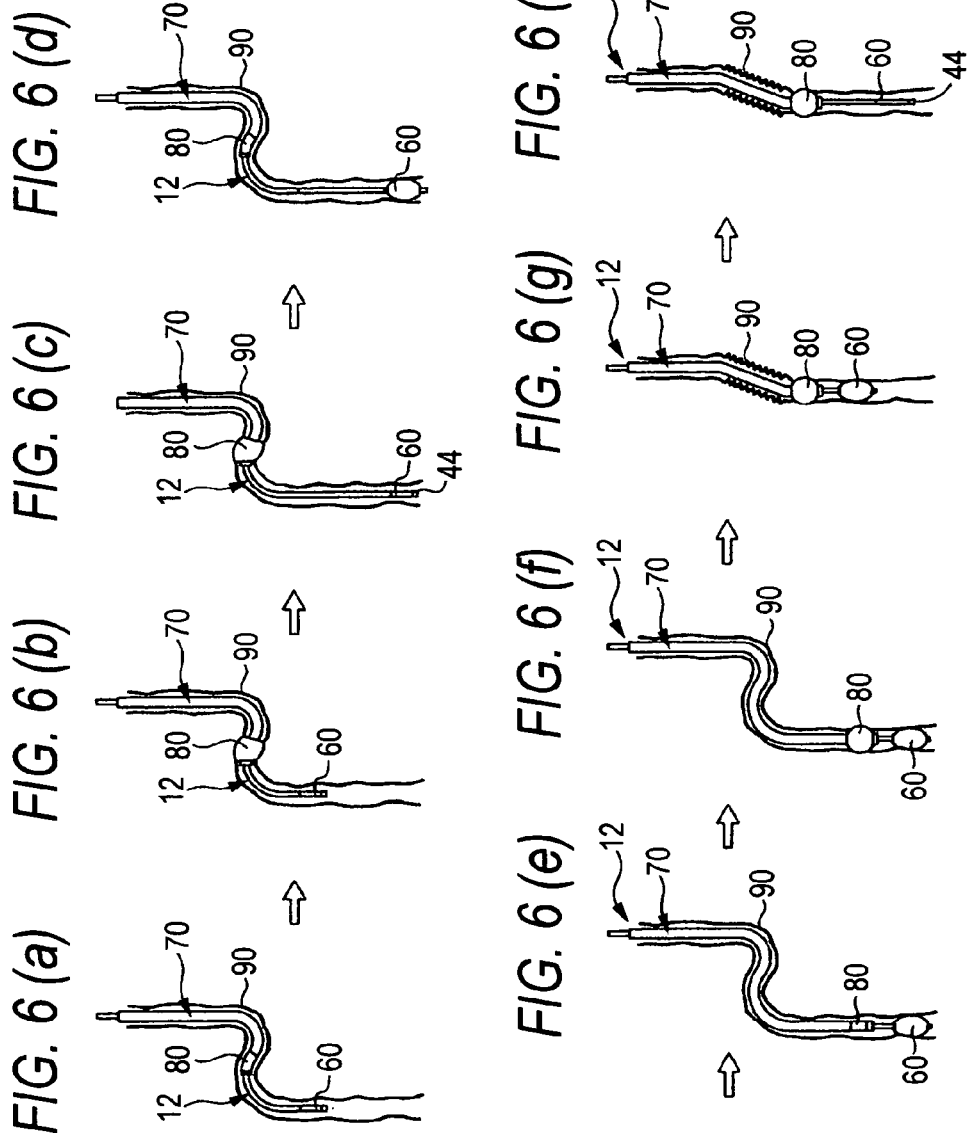
FIGS. 6A to 6H are views showing an operation method of an endoscope apparatus according to the invention.

Next, a description is given of one example of an operation method of the endoscope apparatus based on FIG. 6.

First, as depicted in FIG. 6A, the insertion portion 12 is inserted into an intestinal tract 90 (for example, descending limb of the duodenum) with the insertion assisting member 70 covered on the insertion portion 12. At this time, the first balloon 60 and the second balloon 80 are kept contracted.

Next, as depicted in FIG. 6B, air is supplied into the second balloon 80 for expansion with the distal end of the insertion assisting member 70 inserted into the bending portion of the intestinal tract 90. That is, the switch SW8 of the hand switch 104 is turned on to instruct pressurization, thereby supplying air into the second balloon 80 via the tube 120 from the balloon control unit 100, wherein the second balloon 80 is expanded until the second balloon 80 reaches a predetermined pressurization level. In this state, the second balloon 80 is stopped in the intestinal tract 90, and the distal end of the insertion assisting member 70 is fixed in the intestinal tract 90.

Next, as depicted in FIG. 6C, only the insertion portion 12 of the endoscope 10 is inserted into the depths of the intestinal tract 90. And, as depicted in FIG. 6D, air is supplied into the first balloon 60 for expansion. That is, the switch SW6 of the hand switch 104 is turned on for instructing pressurization, and air is supplied from the balloon control unit 100 via the tube 110. Then, the first balloon 60 is expanded until the first balloon reaches a predetermined pressurization level. Thereby, the first balloon 60 is fixed in the intestinal tract 90.

Next, air is sucked from the second balloon 80 to cause the second balloon 80 to contract. That is, the switch SW8 of the hand switch 104 is turned off for instructing pressure reduction, and air is sucked from the balloon control unit 100 via the tube 120 and the second balloon 80 is caused to contract until the pressure of the second balloon 80 is reduced to a predetermined pressure reduction level. After that, as depicted in FIG. 6E, the insertion assisting member 70 is pushed in and is inserted along the insertion portion 12. And, after the distal end of the insertion assisting member 70 is brought to the vicinity of the first balloon 60, air is supplied into the second balloon 80 as depicted in FIG. 6F to expand the same. That is, by turning on the switch SW8 of the hand switch 104, the second balloon 80 is expanded until it reaches a predetermined pressurization level. Thereby, the second balloon 80 is fixed in the intestinal tract 90. That is, the intestinal tract 90 is grasped by the second balloon 80.

Next, as depicted in FIG. 6G, the insertion assisting member 70 is hauled in, whereby the intestinal tract 90 is made into a contracted state, and excess deflection and bending of the insertion assisting member 70 are removed. Next, as depicted in FIG. 6H, air is sucked from the first balloon 60 to cause the first balloon 60 to contract. That is, pressure reduction is instructed by turning off the switch SW6 of the hand switch 104, and air is sucked from the balloon control unit 100 via the tube 110. The first balloon 60 is caused to contract until the pressure thereof is reduced to a predetermined pressure reduction level.

And, the distal end hard portion 44 of the insertion portion 12 is inserted into the depth of the intestinal tract 90 as much as possible. That is, an insertion operation depicted in FIG. 6C is carried out again. Thereby, it is possible to insert the distal end hard portion 44 of the insertion portion 12 into the depth of the intestinal tract 90. Where the insertion portion 12 is further inserted into the depth, a push-in operation as depicted in FIG. 6E is carried out after a fixing operation as depicted in FIG. 6D is performed, and further, an insertion operation as depicted in FIG. 6F is repeatedly carried out by turns, whereby it is possible to further insert the insertion portion 12 into the depth of the intestinal tract 90.

In this connection, as depicted in FIG. 2, the inlet/outlet port 64 of the air hole through which air is supplied into the first balloon 60 and is sucked is formed so as to pass through a thick portion of the distal end hard portion 44 as depicted in FIG. 3. Also, the inlet/outlet port 64 of the air hole (that is, a discharge/suction axis line 14 of air at the inlet/outlet port 64) is formed to be inclined forward at a predetermined angle ($\theta$) to the axial center 13 of the insertion portion 12.

The inlet/outlet port 64 of the airhole is formed at a position approached the front side portion 61 of the first balloon 60 mounted at the distal end hard portion 44. Also, one end opening portion 152A of the piping member 152 is fitted into and adhered to the opening portion at the inner circumferential side of the inlet/outlet portion 64 of the air hole, and is coupled thereto. The piping member 152 is a corrosion resistant hard pipe formed by bending at a predetermined radius of curvature r, and the distal end portion of a flexible air tube 154 is coupled to the other end opening portion 152B located at a position parallel to the axial center 13 of the insertion portion 12. The piping member 152 is disposed, avoiding a number of contents such as a forceps channel 150, etc., which is disposed in the distal end hard portion 44 as depicted in FIG. 4. A portion from the distal end of the distal end hard portion 44 to the coupling portion between the piping member 152 and the air tube 154 is substantially a hard portion, and the air tube 154 is disposed in the bending portion 42 and the flexible portion 40.

In addition, the piping member 152 of the embodiment is made applicable for a colonoscope the diameter of the distal end hard portion 44 of which is approximately 13 mm, and a fiber scope for the small intestine the diameter of the distal end hard portion 44 of which is approximately 9 mm. Where the radius of curvature of the piping member 152 is r, the attaching angle of the piping member 152 is $\theta$, the height of the piping member 152 from the distal end outer surface is h after the piping member 152 is mounted, and the outer diameter of the distal end hard portion 44 is d, the piping member 152 is formed so as to satisfy the conditions of r>5 mm (preferably 7 mm), $\theta < 60°$ (preferably 30°), and h<d/2.

According to the endoscope 10 having such an inlet/outlet port 64 of the air hole, since the inlet/outlet port 64 is formed to be inclined forward at a predetermined angle 0 to the axial center 13 of the insertion portion 12, insertion of a cleansing brush from the inlet/outlet port 64 of the air hole into the air tube 154 can be facilitated, wherein it becomes possible to cleanse the inlet/outlet port 64 of the air hole and the air tube 154 by means of a brush.

Figure 7:
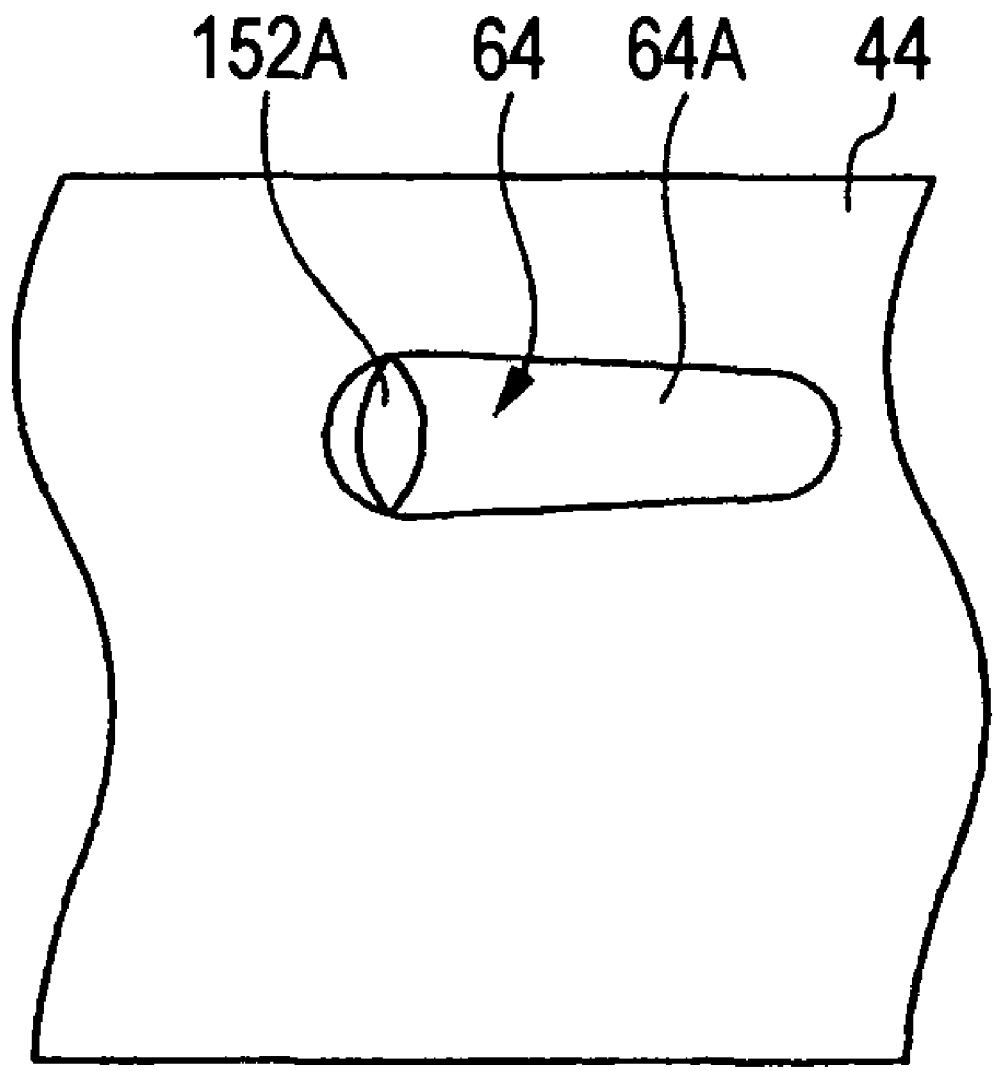
FIG. 7 is an enlarged view depicting the inlet/outlet port of the airhole formed at the distal end hard portion of the endoscope.

Also, since the inlet/outlet port 64 of the air hole is formed to be inclined, the surface opening portion 64A of the inlet/outlet port 64 of the air hole, which appears on the surface of the distal end hard portion 44, becomes a slot (long hole) as shown in FIG. 7. To the contrary, in the inlet/outlet port of the related-art air hole, which is formed in the direction orthogonal to the axial center of the insertion portion, the surface opening portion remains roughly circular even if it is an inlet/outlet portion of the air hole of the same diameter. Since the slot according to the present application is larger than the related-art circular type when the sizes of the surface opening portions are compared with each other, insertion characteristics of a brush can be improved. Furthermore, no air hole is provided at the bending portion 42 because an angle ring or angle rubber, etc., is disposed, wherein it is necessary to provide an air hole at the distal end hard portion. If so, since the surface opening portion 64A of the inlet/outlet port 64 of the air hole is disposed at a position approached to the front side end portion 61 of the first balloon 60, the distance to the first balloon 60 is short, where there is a fear for the first balloon 60 to be adhered to the opening portion 64A when sucking in air. Even in the case, according to the present application in which the surface opening portion is large, there is no case where the entire opening portion 64A is clogged by the first balloon 60 in comparison with the related-art endoscope, wherein air suction characteristics are improved. Still further, as depicted in FIG. 3, since the surface opening portion 64A of the inlet/outlet port 64 of the air hole is secured to be large, a vertical end face 64B is provided, which is obtained by cutting the thickness section of the distal end hard portion 44 located upward of one-end opening portion 152A of the piping member 152 in the vertical direction with respect to the axial center 13.

In addition, the inlet/outlet port 64 of the air hole is connected to the air tube 154 via a piping member 152 bent at a predetermined radius of curvature r. Since the inlet/outlet port 64 of the air hole of the air tube 154 is coupled to the air tube 154 via such a piping member 152, a brush can be smoothly inserted from the inlet/outlet port 64 of the air hole into the air tube 154, wherein it becomes possible to smoothly cleanse the piping member 152 by means of a brush.

Also, a predetermined color is given to a predetermined position 14A of the hand-side operation portion 14 of the endoscope 10 as depicted in FIG. 1, and the same color as the color is given to a predetermined position 70A of the insertion assisting member 70, wherein the insertion assisting member 70 can be distinguished as an insertion assisting member exclusive for the endoscope 10. Therefore, no mistake is brought about in assembly of the endoscope and the insertion assisting member.

With the endoscope apparatus according to the invention, since the inlet/outlet port of the air hole for supplying air into the balloons is formed to be inclined at a predetermined angle to the axis of the insertion portion, a brush can be smoothly inserted into the air tube through the inlet/outlet port of the air hole, wherein it becomes possible to cleanse the inlet/outlet port of the air hole and the air tube by means of a brush.

The entire disclosure of each and every foreign patent application from which the benefit of foreign priority has been claimed in the present application is incorporated herein by reference, as if fully set forth.

What is claimed is:

1. An endoscope apparatus comprising:
   an endoscope comprising an insertion portion, wherein an air hole is formed at a distal end of the insertion portion so as to pass through a distal end hard portion of the insertion portion; and
   a balloon attached to the distal end of the insertion portion, the balloon being expanded by supply of air through an inlet/outlet port of the air hole and contracted by suction of air through of the inlet/outlet port,
   wherein the inlet/outlet port of the air hole is formed to be inclined at a predetermined angle to an axis of the insertion portion of the endoscope, and is connected to an air tube disposed in the endoscope insertion portion via a piping member,
   wherein the inlet/outlet port of the air hole is formed into a slot by cutting a thickness section of the distal end hard portion located upward of one-end opening portion of the piping member,
   wherein the slot of the inlet/outlet port of air hole has
   (i) a surface opening portion which appears on a surface of the distal end hard portion,
   wherein the surface opening portion is larger in dimension than the piping member, and a length in a longitude direction of the surface opening portion is longer than a diameter of the piping member, and
   wherein the surface opening portion is formed on the surface of the distal end hard portion, heights of the surface opening portion edges are substantially equal back and forth in the longitude direction of the insertion portion, and the air hole is formed on an inside of a position of a diameter of the distal end hard portion, and
   (ii) a vertical end face in the vertical direction with respect to the axial center of the insertion portion, and
   wherein the piping member is disposed in the distal end hard portion and is formed by bending at a predetermined radius of curvature ratio so as to smoothly insert a cleansing brush into the piping member.

2. The endoscope apparatus according to claim 1, wherein the piping member is formed so as to satisfy the conditions of r>5 mm, θ<60°, and h<d/2 where a radius of curvature of the piping member is r, an attaching angle of the piping member is θ, height of the piping member from an outer surface of the distal end of the insertion portion is h after the piping member is attached, and an outer diameter of the distal end of the insertion portion is d.

3. The endoscope apparatus according to claim 2, wherein the inlet/outlet port is formed to be inclined forward at said predetermined angle θ with respect to an axial center of the insertion portion.

* * * * *